United States Patent
Phillips

(10) Patent No.: US 6,206,934 B1
(45) Date of Patent: Mar. 27, 2001

(54) ANKLE BLOCK WITH SPRING INSERTS

(75) Inventor: Van L. Phillips, Rancho Santa Fe, CA (US)

(73) Assignee: Flex-Foot, Inc., Aliso Viejo, CA (US)

(*) Notice: Subject to any disclaimer, the term of this patent is extended or adjusted under 35 U.S.C. 154(b) by 0 days.

(21) Appl. No.: 09/138,357

(22) Filed: Aug. 21, 1998

Related U.S. Application Data

(60) Provisional application No. 60/081,472, filed on Apr. 10, 1998.

(51) Int. Cl.$^7$ ............................................. A61F 2/66
(52) U.S. Cl. ......................... 623/53; 623/55; 623/47; 623/49
(58) Field of Search .......................................... 623/47–55

(56) References Cited

U.S. PATENT DOCUMENTS

| | | |
|---|---|---|
| 25,238 | 8/1859 | Bly . |
| 56,983 | 8/1866 | Nicholas . |
| 508,034 | 11/1893 | Moore . |
| 561,979 | 6/1896 | Erickson . |

(List continued on next page.)

FOREIGN PATENT DOCUMENTS

| | | | |
|---|---|---|---|
| 366553 | 1/1923 | (DE) . | |
| 379849 | 8/1923 | (DE) . | |
| 1174328 | 4/1957 | (DE) . | |
| 94444 | 2/1997 | (DE) . | |
| WO 88/06431 | * 9/1988 | (EP) | ........................................ 623/53 |
| 0 401 864 | 12/1990 | (EP) . | |
| WO 96/04869 | 2/1996 | (EP) . | |
| 2640499 | 6/1990 | (FR) . | |
| 621576 | 4/1949 | (GB) . | |
| 1371996 | 10/1974 | (GB) . | |
| 2008410 | * 11/1978 | (GB) | ........................................ 623/53 |
| 806023 | 4/1977 | (SU) . | |
| 778-732 | 8/1977 | (SU) . | |
| 1454-449-A | 11/1986 | (SU) . | |
| 1391-643-A | 4/1988 | (SU) . | |
| 1600759 | 9/1988 | (SU) . | |
| WO 88/88815 | 2/1988 | (WO) . | |

OTHER PUBLICATIONS

Copy of International Search Report.
Product Catalog entitled Campbell Childs, Inc.
Brochure entitled Copes/Bionic Ankle, The Most Significant Development Ankle Prosthetics in Over a Half Century.
G–Foot Prosthesis Installation Manual.
Brochure entitled Carbon Copy HP: High Performance on demand.

*Primary Examiner*—David H. Willse
*Assistant Examiner*—Suzette J. Jackson
(74) *Attorney, Agent, or Firm*—Knobbe, Martens, Olson & Bear, LLP

(57) ABSTRACT

Provided herein is a simple, inexpensive prosthetic foot incorporating an ankle block with spring inserts. The ankle block is formed of compressible material having desired compliance and energy return characteristics. The ankle block is sandwiched between a foot element and an ankle element. One or more spring inserts are embedded inside the ankle block to increase the rigidity of the prosthetic foot and to improve the degree of energy storage and return. The shape of the spring inserts is preferably one that supports compression during relative angular rotation of the ankle plate and foot plate elements, such as during toe and heel roll, and also vertical compression, such as in response to vertical shock loads.

52 Claims, 7 Drawing Sheets

U.S. PATENT DOCUMENTS

| | | |
|---|---|---|
| 619,731 | 2/1899 | Doerflinger et al. . |
| 808,296 | 12/1905 | Merrick . |
| 809,876 | 1/1906 | Wilkins . |
| 817,340 | 4/1906 | Rosenkranz . |
| 1,056,426 | 3/1913 | Kenny . |
| 1,069,001 | 7/1913 | Guy . |
| 2,197,093 | 4/1940 | Campbell . |
| 2,315,795 | 4/1943 | Johnson et al. . |
| 2,556,525 | 6/1951 | Drennon . |
| 2,594,945 | 4/1952 | Lucas et al. . |
| 2,692,392 | 10/1954 | Bennington et al. . |
| 2,731,645 | 1/1956 | Woodall . |
| 3,098,239 | 7/1963 | Nader . |
| 3,551,914 | 1/1971 | Woodall . |
| 3,754,286 | 8/1973 | Ryan . |
| 3,766,569 | 10/1973 | Orange . |
| 3,784,988 | 1/1974 | Trumpler . |
| 3,833,941 | 9/1974 | Wagner . |
| 3,874,004 | 4/1975 | May . |
| 3,982,280 | 9/1976 | Asbelle et al. . |
| 4,091,472 | 5/1978 | Daher et al. . |
| 4,177,525 | 12/1979 | Arbogast et al. . |
| 4,225,982 | 10/1980 | Cochrane et al. . |
| 4,229,839 | 10/1980 | Schwemmer . |
| 4,328,594 | 5/1982 | Campbell et al. . |
| 4,360,931 | 11/1982 | Hampton . |
| 4,463,459 | 8/1984 | Shorter et al. . |
| 4,555,817 | 12/1985 | McKendrick . |
| 4,652,266 | 3/1987 | Truesdell . |
| 4,718,913 | 1/1988 | Voisin . |
| 4,721,510 | 1/1988 | Cooper et al. . |
| 4,892,553 | 1/1990 | Prahl . |
| 4,892,554 | 1/1990 | Robinson . |
| 4,959,073 * | 9/1990 | Merlette ................................ 623/55 |
| 5,007,938 | 4/1991 | Prahl . |
| 5,019,109 | 5/1991 | Voisin . |
| 5,030,239 | 7/1991 | Copes . |
| 5,062,859 | 11/1991 | Naeder . |
| 5,066,305 | 11/1991 | Firth . |
| 5,112,356 | 5/1992 | Harris et al. . |
| 5,116,383 | 5/1992 | Shorter et al. . |
| 5,116,385 | 5/1992 | Allard et al. . |
| 5,156,631 | 10/1992 | Merlette . |
| 5,156,632 | 10/1992 | Wellershaus . |
| 5,181,932 | 1/1993 | Phillips . |
| 5,219,365 | 6/1993 | Sabolich . |
| 5,258,039 | 11/1993 | Goh et al. . |
| 5,290,319 | 3/1994 | Phillips . |
| 5,376,133 | 12/1994 | Gramnas . |
| 5,376,140 | 12/1994 | Ryan . |
| 5,405,411 * | 4/1995 | McCoy .................................. 623/49 |
| 5,443,527 | 8/1995 | Wilson . |
| 5,701,686 | 12/1997 | Herr et al. . |
| 5,728,177 | 3/1998 | Phillips . |
| 5,800,569 * | 9/1998 | Phillips ................................ 623/53 |
| 5,888,239 | 3/1999 | Wellershaus et al. . |
| 5,913,902 * | 6/1999 | Geible .................................. 623/55 |
| 5,941,913 * | 8/1999 | Woolnough et al. .................. 623/47 |

* cited by examiner

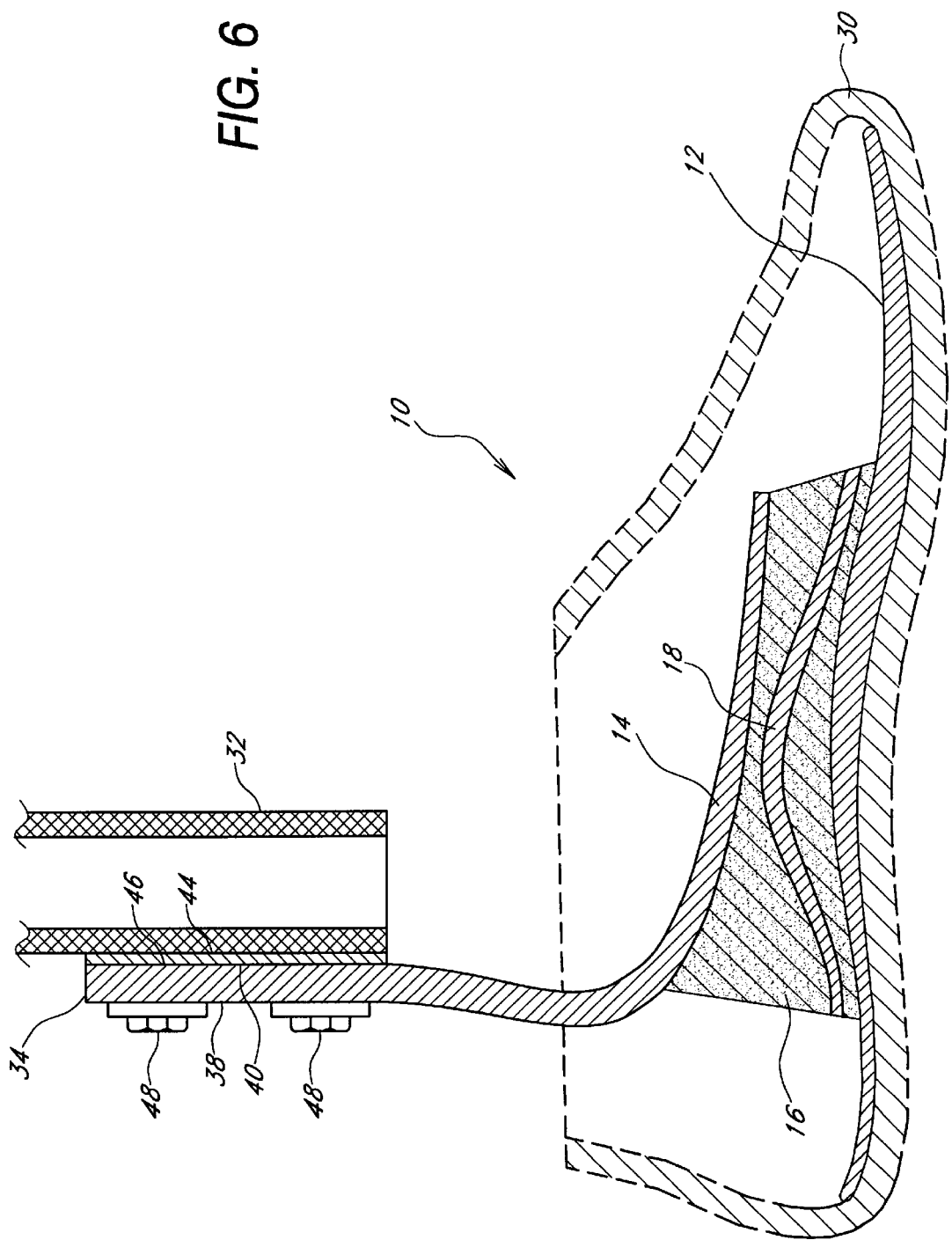

ANKLE BLOCK WITH SPRING INSERTS

CROSS-REFERENCE TO PENDING APPLICATION

This application is a continuation of provisional application Ser. No. 60/081,472, filed Apr. 10, 1998.

BACKGROUND OF THE INVENTION

1. Field of the Invention

The present invention relates to prosthetic feet and, more particularly, to a simply constructed, low-profile prosthetic foot having enhanced performance characteristics.

2. Description of the Related Art

In the prosthetics market, the conventional SACH (solid-ankle, cushion-heel) foot has been the most widely prescribed artificial foot over the past 35 years. The SACH foot generally includes a solid ankle and cushioned heel foot mounted to a limb along an approximate hinge axis taken through the ankle. The SACH foot has been popular precisely for its simplicity, and thus economy, but includes certain drawbacks in terms of dynamic response characteristics. Specifically, the low end SACH feet do not provide much energy storage and release, as do more sophisticated prosthetic feet.

Most modern foot prostheses incorporate some form of energy storage element for storing and releasing walking energy. Conventionally, this might consist of a spring-loaded ankle joint comprising metal coil springs or, more commonly, rubber compliance members. Inexpensive foot prostheses have also been devised having essentially a solid rubber or foam ankle block for storing and releasing walking energy. Such an ankle block has been disclosed in my issued patent titled PROSTHESIS WITH RESILIENT ANKLE BLOCK, U.S. Pat. No. 5,800,569, the entirety of which is incorporated by reference. A solid, compressible ankle block may be secured between upper and lower support members to provide resilient compression and energy storage and release. The use of an ankle block member provides significant manufacturing and cost advantages. However, for certain applications it is difficult to attain a desired level of spring compliance and energy return characteristics using a solid ankle block due to the inherent limitations of the materials involved in terms of elasticity, viscosity and maximum compression.

Therefore, it would be desirable to provide an ankle block having selectable compliance and energy return characteristics that may be varied over a wider range to accommodate the different weight, height and activity levels of amputees.

SUMMARY OF THE INVENTION

In response to the problems with the prior art, the present invention provides a simple, inexpensive prosthetic foot incorporating an ankle block with spring inserts. The ankle block is formed of compressible material having desired compliance and energy return characteristics. The ankle block is sandwiched between a foot element and an ankle element. One or more spring inserts are embedded inside the ankle block to increase the rigidity of the prosthetic foot and to improve the degree of energy storage and return. The shape of the spring inserts is preferably one that supports compression during relative angular rotation of the ankle plate and foot plate elements, such as during toe and heel roll, and also vertical compression, such as in response to vertical shock loads.

In one aspect of the present invention, a basic prosthetic foot is provided having enhanced performance characteristics generally comprising a lower foot plate, an upper ankle plate, a foam ankle block joining the two plates, and a spring element embedded in the ankle block. Both the foot plate and the ankle plate are constructed of strong, flexible material, preferably a laminate of composite material. The foot plate is sized approximately equal to a human foot being replaced, while the ankle plate has a similar width, but has a shorter length than the foot plate. The ankle block has a length and width approximately equal to the ankle plate and is aligned therewith. The spring element comprises two relatively flat carbon fiber composite members secured at their middle and separated at their ends. This gives the spring element a preferable shape of a bowtie or double wishbone. Preferably, an attachment member couples the ankle plate to a stump or lower-limb pylon of the wearer. During walking, the combination of the resilient ankle block with embedded spring element and flexible plates provides a smooth rollover from a heel-strike to a toe-off position.

In another aspect, the ankle block of a prosthetic foot may be provided with cylindrical openings both in the fore and aft positions of the ankle block. These openings enable the placement of additional inserts or stiffeners to give the block a desired rigidity. In a preferred embodiment, the foot element also has a tapered thickness. Further, the foot element comprises uplifted heel and toe ends and an arch region therebetween.

Further advantages and applications will become apparent to those skilled in the art from the following detailed description and the drawings referenced herein.

BRIEF DESCRIPTION OF THE DRAWINGS

FIG. 6 is a cross-sectional view of an alternative embodiment of the prosthetic foot of the present invention.

DETAILED DESCRIPTION OF THE PREFERRED EMBODIMENTS

Figure 1:
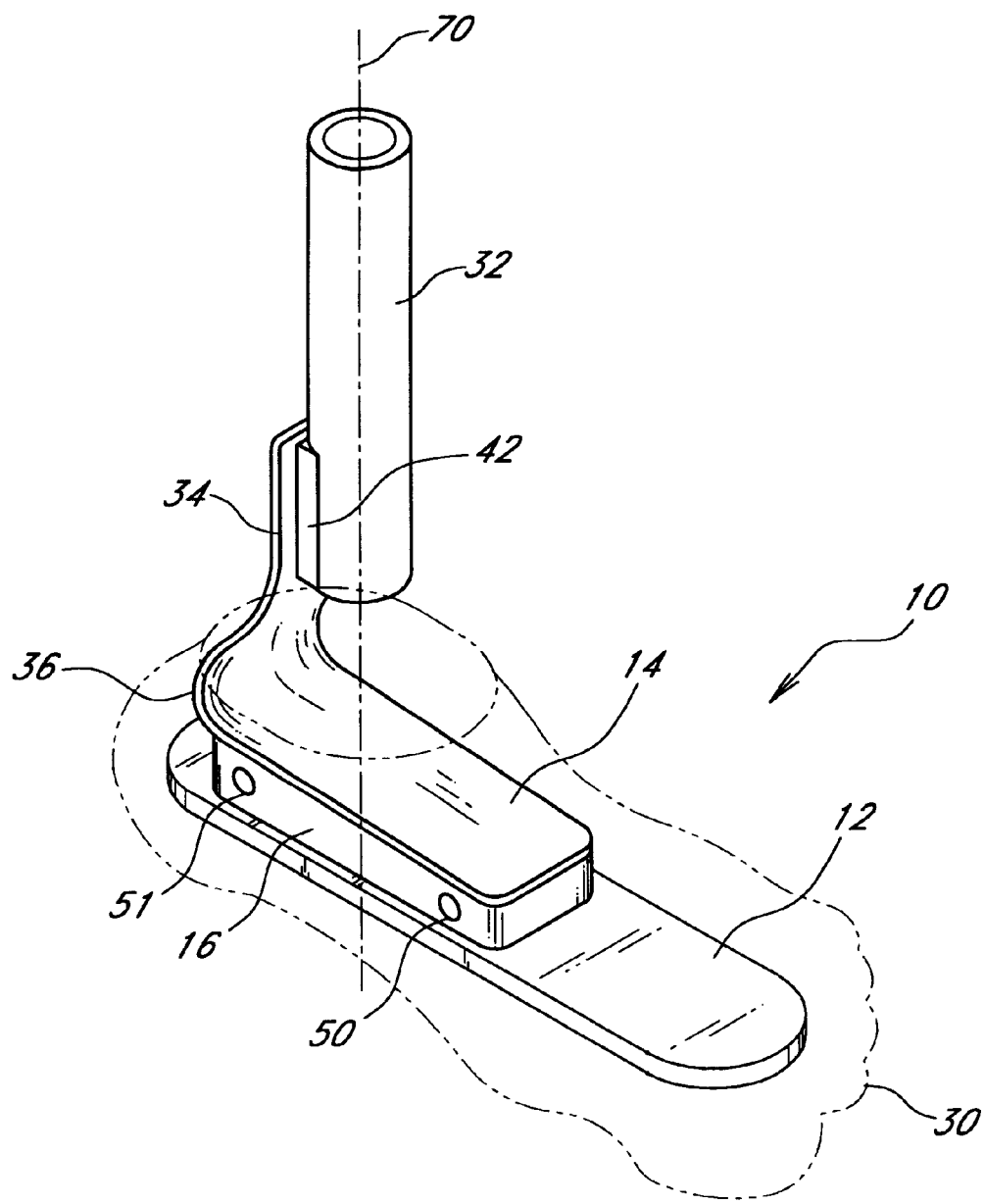
FIG. 1 is a perspective view of the prosthetic foot of the present invention.
Figure 2:
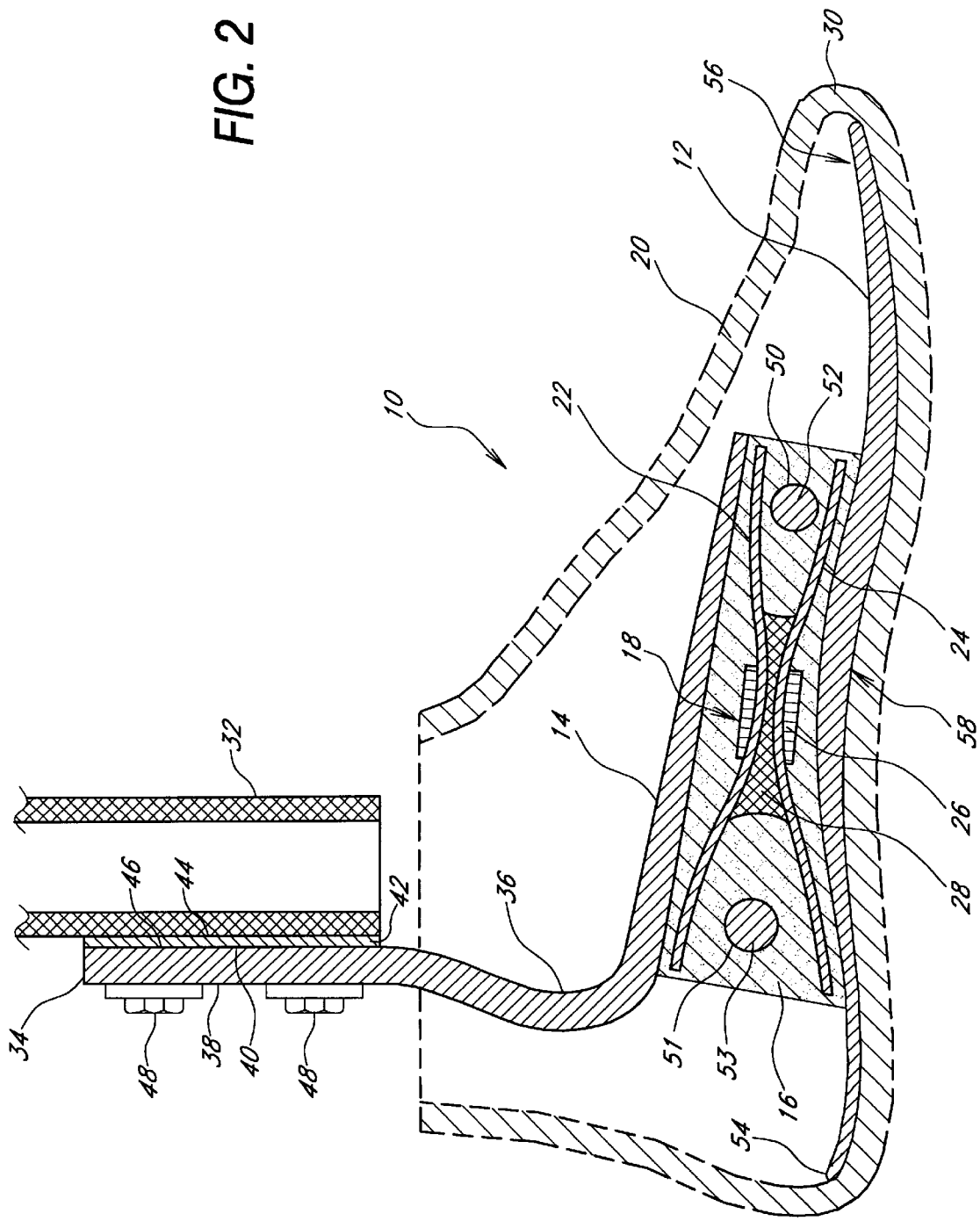
FIG. 2 is a cross-sectional view of the prosthetic foot of the present invention.

With reference to FIGS. 1 and 2, a first embodiment of a prosthetic foot 10 of the present invention is shown in a perspective view and a cross-sectional side view, respectively. The prosthetic foot 10 generally comprises a lower foot plate 12 an upper, smaller ankle plate 14, an ankle layer or block 16 made of resilient material, connecting the foot plate 12 to the ankle plate 14, and a spring element 18 embedded within the ankle block 16. The foot plate 12 has a length and width roughly equal to the approximate length and width of the particular wearer's amputated foot and sized to fit within an outer, flexible cosmesis 30, shown in phantom. The ankle plate 14 and the resilient ankle block 16 have approximately the same horizontal cross-sectional size. The ankle plate 14, ankle block 16, and spring element 18 are centered transversely with respect to and are generally positioned over the back half of the foot plate 12. The ankle block 16 is sandwiched between the foot plate 12 and the ankle plate 14 and is preferably glued or bonded to both plates using polyurethane adhesive or other known securement technologies.

Figure 3:
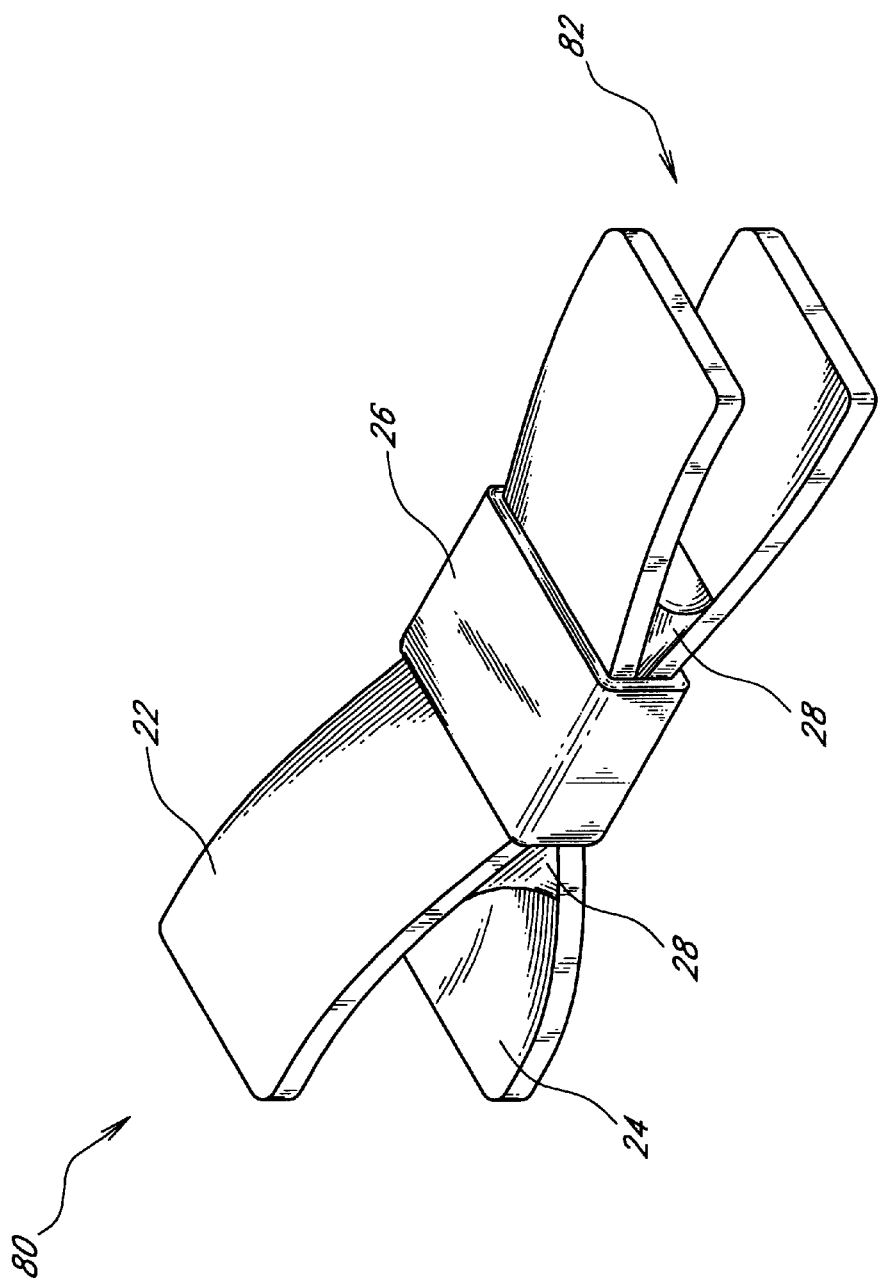
FIG. 3 is a perspective view of the spring element embedded in the ankle block of the present invention.

The spring element 18 is a resilient support member inserted within the resilient ankle block 16. As shown in FIG. 3, the spring element 18 is preferably comprised of upper and lower plate-like members 22 and 24, each of which is relatively flat and has a substantially rectangular vertical projection. These members are secured at their center by a fastener 26 and separated at ends 80 and 82. The upper member 22 preferably has a curvilinear concave upward shape, while the lower member 24 preferably has a curvilinear concave downward shape. This gives the spring element 18 a substantially double wishbone or bowtie shape.

As shown in FIG. 1, the spring element 18 is completely embedded within the ankle block 16 so as not to be visible from the outside. Referring to FIG. 2, the spring element 18 extends substantially longitudinally across the length of the ankle block 16, and has a width substantially equal to the width of ankle block 16. The fastener 26 may comprise bolts, a weld, or any other fastening means as would be known to those skilled in the art. In the preferred embodiment, the fastener 26 is a strap which is laminated around the center portion of the two members 22, 24. A wedge member 28, preferably of a resilient elastomer, is placed between the two plate members 22, 24 to protect the inner surfaces of the members and to provide additional support to the spring element 18. The wedge 28 acts to provide leverage between the two plate members 22, 24, and enables adjustment of the flexing characteristics of the spring element 18, if desired. Alternatively, it may be bonded permanently in place or formed integrally with one or both of the plate members 22, 24, as desired. Although the spring element 18 has been described as having a double wishbone or bowtie configuration, other shapes and sizes may be appropriate for providing support to the ankle block 16. Furthermore, more than one spring element may be provided in the ankle block to provide support and energy return to the prosthetic foot 10.

As can be seen in FIGS. 1 and 2, the prosthetic foot 10 further comprises a pylon member 32 which can be secured to the stump of the amputee (not shown) and extends relatively downward therefrom in a generally vertical direction. The pylon member 32 in the preferred embodiment is of tubular construction having a substantially equal moment of inertia in all directions to restrict bending in all directions. The tubular member 32 is also preferably hollow so that it is relatively light in weight and utilizes less material which reduces the cost of production. The pylon member 32 is dimensioned so as to be interchangeable with a standard 30 mm pylon. Other configurations which impart rigidity, such as rectilinear cross sections having relatively larger moments of inertia about one or both transverse axes can also be utilized to obtain the benefits discussed herein. A centerline 70 through pylon 32, shown in FIG. 1, defines the downward direction of the application of force.

As shown in FIGS. 1 and 2, the ankle plate 14 is secured to the pylon member 32 through a vertically oriented upper attachment member 34. The upper attachment member 34 is attached to a curvilinear ankle section 36, which is connected to the ankle plate 14. Preferably, these three pieces are monolithically formed with one another for optimum strength and durability. The attachment member 34 has a rearward surface 38, as shown in FIG. 2, and a forward surface 40 substantially parallel thereto. The attachment member 34 is substantially rigid and capable of sustaining torsional, impact and other loads impressed thereupon by the prosthesis. In addition, the inherent rigidity of attachment member 34 prevents it from being distorted in any substantial way and causes the effective transmission of the aforesaid loads imposed thereupon to a suitable ancillary prosthetic pylon 32.

With reference to FIG. 2, the attachment member 34 is in the preferred embodiment vertically oriented so that it may be secured to the pylon member 32. A coupling device 42 is positioned at the lower end of the pylon member 32 which provides a flat surface upon which the vertical attachment member 34 can be secured. The coupling device 42 has one attachment surface 44 which mates with the cylindrical outer surface of the pylon member 32 and a second substantially flat attachment surface 46 which mates with the attachment member 34. In the preferred embodiment, attachment surface 44 is curved to closely mate with the outer surface of the tubular pylon member 32, and attachment surface 46 is flat to accommodate the forward surface 40 of the attachment member 34.

Desirably, the coupling device 42 is welded or bonded to the pylon member 32 and has two holes (not shown) into which two bolts 48 can be inserted and secured. The attachment member 34 also has two holes (not shown) which align with the holes on the coupling device to place and secure the two bolts 48 through the attachment member 34 and the coupling device 42. Other methods of securing the pylon member to the foot portion are contemplated, such as those disclosed in my prior issued U.S. Pat. No. 5,514,186, the entirety of which is incorporated by reference, as well as those utilizing integrally formed constructions.

As stated, the attachment member 34 monolithically formed with the ankle plate 14 is vertically aligned so that it extends relatively downward from the coupling device 42 on the pylon member 32. As shown in FIG. 2, the thickness of the attachment member 34 along this vertical section is relatively greater than the thickness of the ankle plate 14 substantially horizontally aligned along the foot portion. The attachment member 34 is also made relatively thicker to support the vertical load imposed on the prosthetic device as well as to restrict undue bending at this juncture. The entire upper vertically-aligned section of attachment member 34 is preferably of substantially uniform thickness and width.

The tubular pylon member 32 is preferably removable from the prosthetic device such that the pylon member can be replaced without replacing the remainder of the prosthetic device. This permits Applicant's invention to be utilized in a broader range of applications. For instance, the tubular member of Applicant's invention can be cut and adapted for use by amputees having different stump lengths including growing amputees. The prosthetist merely needs to cut a standard tubular pylon to the appropriate length. Moreover, this eliminates the need to manufacture as a part of the prosthesis a long rigid leg section. Thus, fewer materials are needed to manufacture the prosthesis of Applicant's invention resulting in reduced manufacturing costs.

The preferred embodiment further comprises cylindrical slots or openings 50, 51 in the fore and aft portions of the ankle block 16, respectively, as shown in FIG. 2, to accommodate insertion of stiffeners 52, 53. The cylindrical openings 50, 51 are disposed horizontally in a direction generally transverse to a forward walking motion, and between upper and lower plate members 22 and 24. Stiffeners 52, 53 can be removably placed in these openings to provide additional support and rigidity to the prosthetic foot 10, and also to modify the spring characteristics of the prosthetic foot. For instance, additional energy storage and return can be provided for a more active amputee by inserting stiffeners 52, 53 into ankle block 16 having a higher spring constant. On the other hand, when more control is desired, stiffeners with a lower spring constant may be inserted to produce an ankle block 16 with greater dampening characteristics. Alternatively, the cylindrical openings 50, 51 may remain empty, thereby making the compliance characteristics dependent solely on the ankle block 16 and the spring element 18.

Preferred Materials and Fabrication

Both the foot plate 12 and the ankle plate 14 are preferably formed of a flexible material so that flexing of the plates tends to relieve extreme shear stresses applied to the interfaces between the ankle block 16 and the plates 12, 14. Both the foot plate 12 and the ankle plate 14 are preferably constructed of fiberglass which provides strength and flexibility. The preferred material for the ankle plate 14 and the foot plate 12 is a vinyl ester based sheet molding compound, such as Quantum #QC-8800, available from Quantum Composites of Midland, Mich. Alternatively, the plates may be formed by a plurality of lamina embedded in an hardened flexible polymer. In other arrangements, the plates may be formed of other materials such as carbon fiber composites as may be apparent to one skilled in the art. The desirable properties of the plates are that they are relatively resilient so as to withstand cracking upon application of repeated bending stresses yet have sufficient flexibility to enhance the performance characteristics felt by the wearer in conjunction with the properties of the resilient ankle block. The pylon member 32 is preferably made of a stiff material such as a laminate of fiber reinforced composite. Stiffness in the pylon member 32 can also be provided by a stiffer and more dense material.

The ankle block 16 is sandwiched between the foot plate 12 and the ankle plate 14 as shown in FIGS. 1 and 2 and is preferably bonded to both plates. The ankle block is preferably formed of urethane, rubber or other suitable material having desired compliance and energy return characteristics. A preferred material for the ankle block is expanded polyurethane foam such as cellular Vulkolka® Pur-Cell No. 15-50, with a density of approximately 500 kg/m$^3$ as available from Pleiger Plastics Company of Washington, Pa. Alternatively, the ankle block 16 may be molded or fabricated from a wide variety of other resilient materials as desired, such as natural or synthetic rubber, plastics, honeycomb structures or other materials. Cellular foam, however, provides a high level of compressibility with desirable viscoelastic springiness for a more natural feeling stride without the stiffness drawbacks and limited compression associated with solid elastomeric materials. Furthermore, the cellular nature of a foam block makes it lighter than solid elastomers. Foam densities between about 150 and 1500 kg/m$^3$ may be used to obtain the benefits of the invention taught herein.

The spring element 18 is preferably made from a highly resilient material that is capable of supporting compression during relative angular rotation of the upper and lower members 12 and 14, such as during toe and heel roll, and also vertical compression such as in response to vertical shock loads. One preferred material is carbon fiber composites such as woven fiber mats and chopped fiber in an epoxy matrix. However, other materials with similar strength and weight characteristics will be known to those skilled in the art and may be used with efficacy. For instance, other filament types may be used, such as glass, Kevlar and nylon by way of example, to ensure lightweight and structural and dynamic characteristics consistent with the needs of a particular amputee. The wedge 28 may be fabricated from a wide variety of resilient materials, including natural and synthetic rubber, elastomeric polyurethanes, or the like.

The ankle block 16 containing spring element 18 may be fabricated by injecting a polyurethane elastomer into a mold allowing it to cure. The spring element 18 may be inserted into the mold prior to injection of the polyurethane so that during curing, the polyurethane bonds to the spring member. Cylindrical slots or openings 50, 51 for insertion of stiffeners 52, 53 may be provided in ankle block 16 by inserting cylindrical plugs into the block prior to injection of polyurethane. Alternatively, openings may be provided in the block after curing simply by cutting or drilling away portions of the ankle block.

The stiffeners provided in the openings are preferably tubes of foam material having a density chosen according to desired compliance characteristics. A preferable material is expanded polyurethane having a foam density between about 150 and 1500 kg/m$^3$. More preferably, a density of about 250 to 750 kg/m$^3$ is preferred to provide adequate adjustment of the energy storage and return characteristics of the prosthetic foot.

Preferred Dimensions

Figure 4:
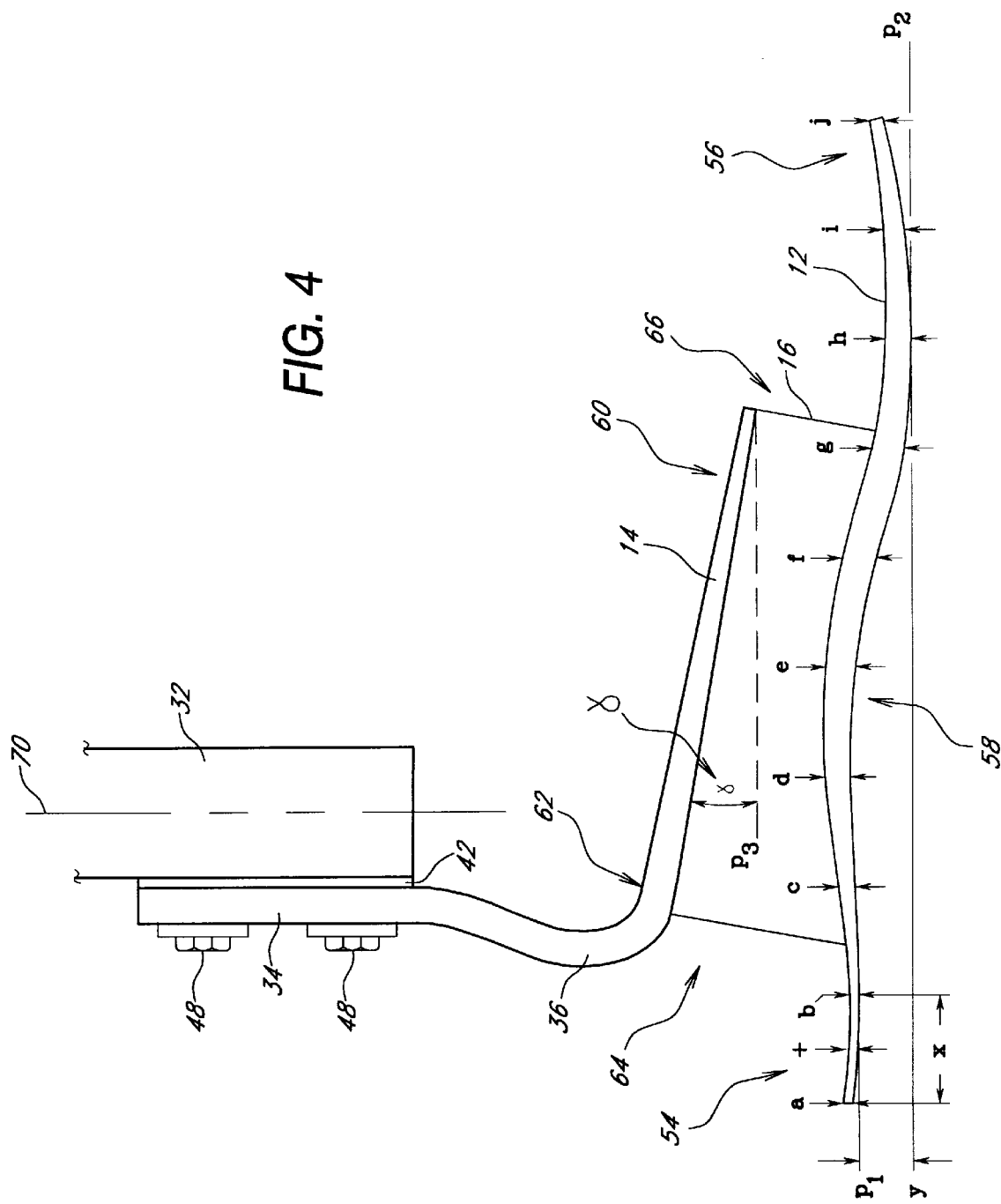
FIG. 4 is a side elevational view of the prosthetic foot more clearly showing a foot plate having a tapered thickness along its length.

As illustrated in FIG. 4, the foot plate 12 is preferably of curvilinear shape. The thickness t of foot plate 12 is preferably tapered along its length, and the tapered profile corresponds approximately to the weight of the amputee. That is, for a heavier amputee, the thicknesses along the length would be greater than for a lighter weight amputee. Generally, the weight groups may be classified as light, medium, or heavy.

Table I below presents preferred groupings, as module sizes C/D/E, of cosmesis sizes corresponding to a male "A" width shoe last. The sizes are presented by length L, width B at the forefoot and width H at the heel of the cosmesis.

TABLE I

Cosmesis Sizes for Male "A" Width Shoe Last

| MODULE | LENGTH L (cm) | WIDTH B (cm) | WIDTH H (cm) |
| --- | --- | --- | --- |
| C | 22 | 2.88 | 2.19 |
|  | 23 | 3.00 | 2.25 |
|  | 24 | 3.12 | 2.31 |
| D | 25 | 3.25 | 2.44 |
|  | 26 | 3.38 | 2.50 |
|  | 27 | 3.50 | 2.56 |
| E | 28 | 3.62 | 2.69 |
|  | 29 | 3.75 | 2.75 |
|  | 30 | 3.88 | 2.81 |

Table II below presents preferred module sizes for various weight groups of amputees.

TABLE II

Modules vs. Weight Groups

| MODULE | WEIGHT GROUP | | |
|---|---|---|---|
| | LIGHT | MEDIUM | HEAVY |
| C | CL | CM | — |
| D | DL | DM | DH |
| E | — | EM | EH |

Table III below presents preferred taper thicknesses (t) for an average or "DM" size foot plate 12 taken at positions spaced by distance x=1 inch (2.54 cm).

TABLE III

Taper Thickness t for DM Foot Plate

| POSITION (x = 2.54 cm) | THICKNESS t (cm) |
|---|---|
| a | 0.16 |
| b | 0.16 |
| c | 0.32 |
| d | 0.52 |
| e | 0.69 |
| f | 0.78 |
| g | 0.71 |
| h | 0.60 |
| i | 0.48 |
| j | 0.28 |

The foot plate 12 has a heel end 54, toward the left in FIG. 4, which is concave-upward or slightly uplifted from a horizontal plane $P_1$ tangential to the heel end 54 of the foot plate 12. Similarly, a toe end 56, to the right of FIG. 4, is concave upward or somewhat uplifted from a horizontal plane $P_2$ tangential to the front portion of the foot plate 12. An arch section 58 is formed between the heel and toe ends and is preferably concave-downward, as shown.

It is understood that within the cosmesis 30 (not shown), the tangent plane $P_1$ of the heel end 54 is slightly raised a distance y relative to the tangent plane $P_2$ of the toe end 56, as shown. The DM-sized foot plate of Table III, for example, has y=0.5 inches (1.27 cm). The foot plate 12 is preferably 0.25 inches (0.63 cm) from the bottom or sole of the cosmesis 30. The cosmesis 30 may be insert molded using an anatomically sculpted foot shape, with details and sizing based on a master pattern and/or digitized data representing typical foot sizes.

An intermediate region 58 comprising the arch portion of the foot plate 12 has the greatest thickness of the foot plate 12. The curvature of the arch region 58 is defined by the cosmesis or shoe sole profile, and generally corresponds to selected ranges of human foot lengths.

The foot plate 12 of prosthesis 10 preferably has a length between about 5 and 15 inches (about 13 and 38 cm), more preferably between about 8 and 12 inches (about 20 and 30 cm) for the foot sizes given in Table I. The width of foot plate 12 is preferably about 1 to 4 inches (about 2.5 to 8 cm). For the example given in Table III for a DM-sized foot plate 12 the length of the plate 12 is approximately 9 inches (about 23 cm) and its width is about 2 inches (about 5 cm). The foot plate 12 has a thickness between about 0.05 and 0.4 inches (about 0.1 and 1 cm), which more preferably may be tapered as indicated in Table III.

The ankle plate 14 of prosthesis 10 is substantially planar, and is preferably shorter in length than the foot plate 12 and has a thickness also defined by the weight group of the wearer. The thickness of the ankle plate is preferably about 0.05 to 0.4 inches (0.1 to 1 cm). More preferably, the corresponding ankle plate 14 in the present example is about 0.2 inches (about 0.5 cm) thick at rear portion 62, tapering to a thickness of about 0.1 inches (about 0.25 cm) at front portion 60. The ankle plate 14 preferably has a length of about 3 to 7 inches (about 8 to 18 cm) and a width of about 1 to 3 inches (about 2.5 to 8 cm), more preferably having length-width dimension of approximately 5×2 inches (about 13×5 cm). The ankle plate 14 is positioned at an angle such that its front tip 60 is located closer to the foot plate 12 than its rear tip 68. Relative to plane $P_3$ shown in FIG. 4, the rear tip is preferably raised an angle γ of about 5 to 30 degrees, and more preferably, about 10 degrees.

The ankle block 16 is generally sized such that its upper surface is planar and corresponds to the length and width of the ankle plate 14. The lower surface of the ankle block 16 is substantially curvilinear to mate with the curvilinear surface of foot plate 12. In the present example, the block 16 has a preferred thickness, at its front 66, of about 1 to 3 inches (about 2.5 to 8 cm), more preferably about 1.3 inches (about 3.4 cm). Its thickness tapers to a minimum of about 0.5 to 1 inch (about 1 to 2.54 cm), more preferably about 0.8 inches (about 2 cm) adjacent arch portion 58. The rear 64 of the block 16 is preferably about 1 to 4 inches (about 2.5 to 10 cm) thick, more preferably about 2.6 inches (about 6.6 cm) thick, which is about twice the thickness of the front portion 66 of the block 16. This gives the ankle block a substantially wedge shape. The greater thickness at the rear of block 16 is provided to impart additional support in the rear portion 64 of the ankle block due to greater compressive forces on the rear of the foot prosthesis caused by off-axis application of force relative to axis 70 during heel strike (see FIG. 5A).

The ankle block 16 may be provided in varying heights or thicknesses, as desired, but is most effective with a thickness of between about 1 and 4 inches (about 2.54 and 10 cm). The front portion and rear surfaces of ankle block 16 are preferably angled according to the angle γ defined by the plane $P_3$ and the ankle plate 14. In other words, the ankle block has front and rear surfaces which are preferably sloped forward at an angle γ from vertical. The ankle block thus provides a relatively stiff, yet flexible ankle region which can be customized for various wearers. Heavier wearers may require a denser resilient material for the ankle block, while lighter wearers may require a less dense material or less thickness.

As shown in FIGS. 2 and 3, the spring element 18 is positioned in the ankle block such that the center of the spring element 18, at the position of fastener 26, is located approximately above the arch portion 58 of foot plate 12. The two members 22, 24 of the spring element 18 preferably have a constant thickness of about 0.05 to 0.2 inches (about 0.1 to 0.5 cm). The distance between the two members at front end 82, when no load is impressed onto the foot 10, is preferably about 0.5 and 2 inches (about 1 to 5 cm), more preferably about 0.7 inches (about 1.8 cm). At rear end 80, when no load is impressed on the foot 10, the distance between members 22 and 24 is about 1 to 3 inches (about 2.5 to 7.5 cm), more preferably about 1.4 inches (about 3.5 cm). As described in further detail below, when the foot is in a heel-strike position, the rear end 80 of the spring element is compressed. When the foot is in a toe-off position, the forward end 82 of the spring element is compressed.

The lengths, widths and thicknesses of the foot plate 12 ankle plate 14, ankle block 16 and spring element 18 may be customized for the wearer according to his/her foot size as well as the approximate weight group of the wearer. Likewise, the material choice and size for these elements may be varied according to the wearer's foot size and weight.

The cylindrical openings 50, 51 provided in the fore and aft portions of ankle block 16 preferably have a diameter of about 0.1 to 0.4 inches (about 0.25 to 1 cm), and more preferably, about 0.2 inches (about 0.5 cm). While the openings 50 and 51 shown in FIG. 2 have the same diameter, the diameters of the openings may be different to accommodate different sized stiffeners. For instance, the diameter of opening 51 may be made larger than the diameter of opening 50 to correspond with the greater volume of ankle block 16 in rear portion 64.

Performance Characteristics

Figure 5A:
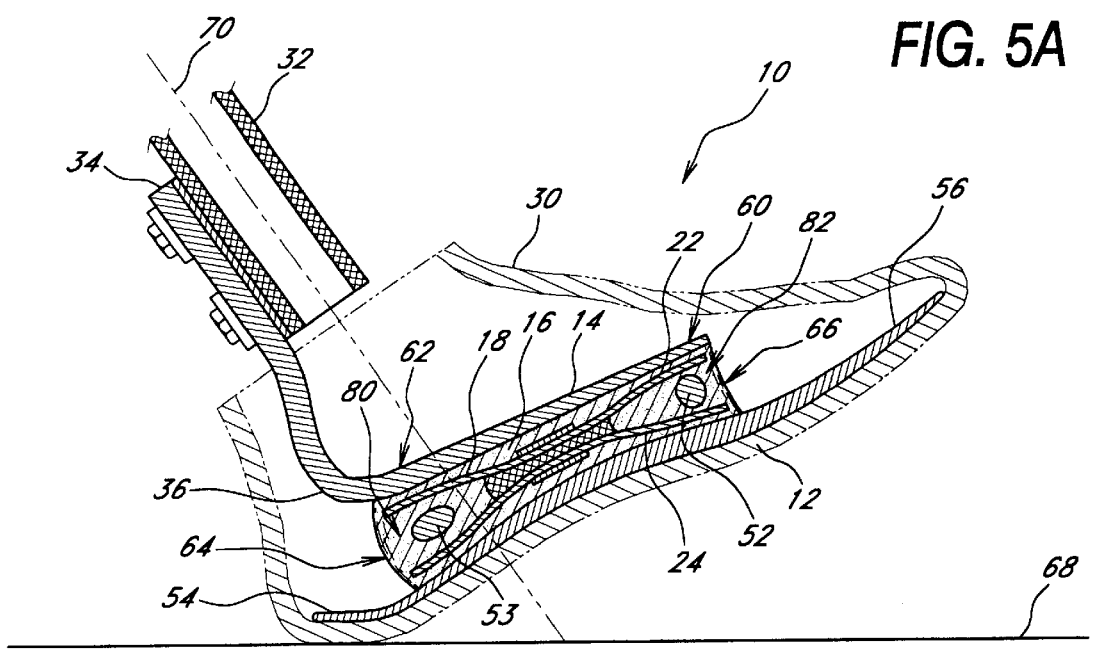
FIG. 5A is a sectional view of the prosthetic foot in a heel-strike position of a walking stride.
Figure 5B:
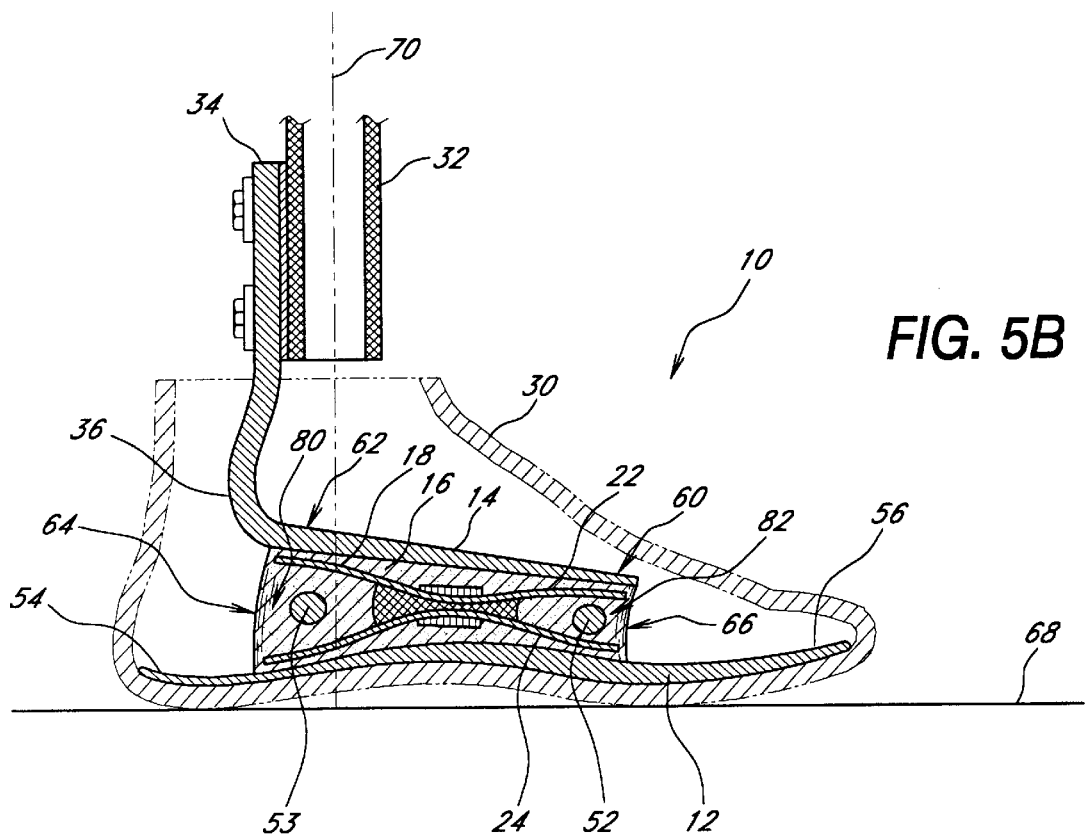
FIG. 5B is a sectional view of the prosthetic foot in a flat position of a walking stride.
Figure 5C:
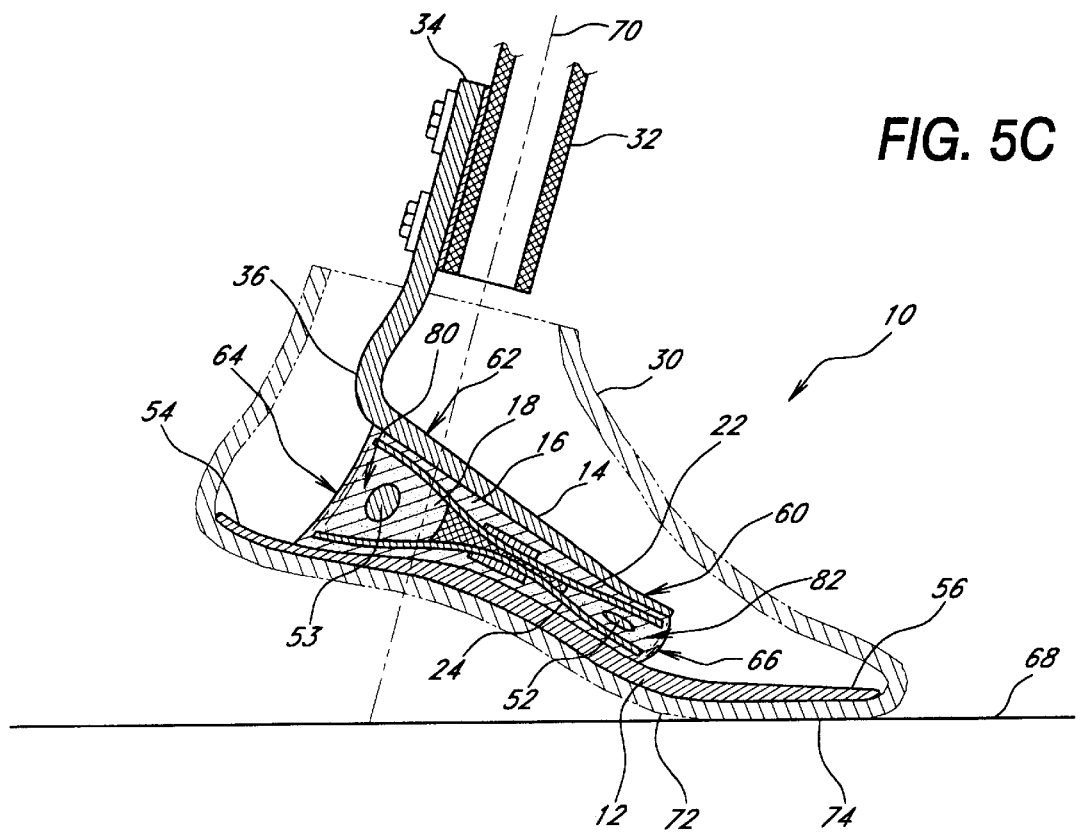
FIG. 5C is a sectional view of the prosthetic foot in a heel-off position of a walking stride.
Figure 5D:
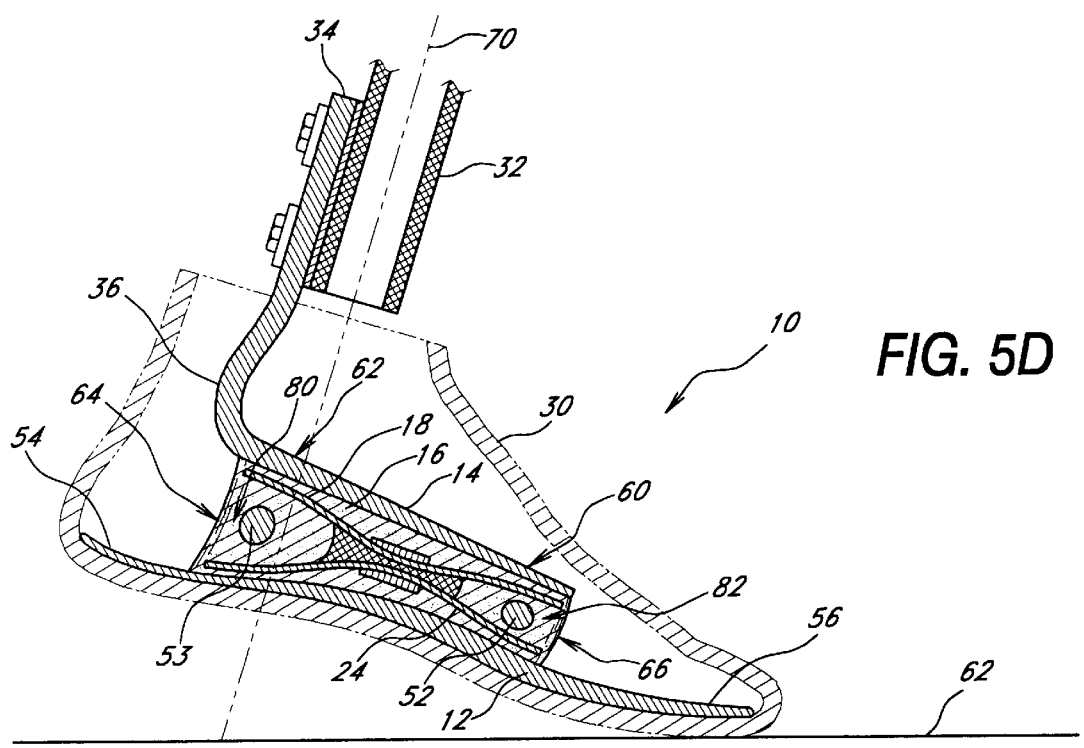
FIG. 5D is a sectional view of the prosthetic foot in a toe-off position of a walking stride.

To more fully explain the improved performance characteristics of the present prosthetic foot 10, FIGS. 5A–5D show "snapshots" of a prosthetic foot in several positions of a walking stride. More particularly, FIG. 5A shows a heel-strike position, FIG. 5B shows a generally flat or mid-stance position, FIG. 5C shows a heel-off position, and FIG. 5D shows a toe-off position. Throughout the various positions shown for a walking stride, the present prosthetic foot 10 provides a smooth and generally life-like response to the wearer. During a walking stride, the ankle block 16 transmits the forces imparted thereon by the foot plate 12 and ankle plate 14, and experiences a gradual rollover, or migration of the compressed region, from rear to front.

With specific reference to FIG. 5A, a first position of a walking stride generally entails a heel strike, wherein the wearer transfers all of his or her weight to the heel of the leading foot. In this case, a rear portion 54 of the foot plate 12 comes in contact with a ground surface 68, albeit through the cosmesis 30. The flexible nature of the foot plate 12 allows it to bend slightly in the rear portion 54, but most of the compressive stresses from the weight of the wearer through the prosthetic foot 10 to the foot plate 12 are absorbed by a rear region 64 of the ankle block 16 with spring element 18. The spring element 18 in the rear portion contracts, such that the distance between members 22 and 24 at rear end 80 decreases. In a front region 66 of the ankle block 16, the spring element 18 may expand slightly such that the distance between members 22 and 24 at front end 82 increases. Front portion 66 of the ankle block 16 experiences a stretching, or tension, due to the attachment along the entire lower edge of the ankle block with the foot plate 12 while rear portion 64 experiences compression. The contraction of the spring element 18 at end 80 and ankle block 16 at end 64 allows the prosthesis 10 to absorb and store energy from the compressive stresses during heel strike. Further, a slight amount of bending may occur in a rear region 68 of the ankle plate 14. The rear stiffener 53 between members 22 and 24 is compressed so as to provide necessary support to the foot prosthesis and to prevent separation of the members 22, 24 from the wedge 28. Front stiffener 52 is slightly stretched substantially vertically due to the tension forces at front portion 66 of ankle block 16.

Next, in FIG. 5B, the wearer reaches a generally flat-footed or mid-stance position, whereby the foot plate 12 contacts the ground 68 along substantially its entire length, again through the cosmesis 30. In this position the weight of the wearer is directed substantially downwardly, so that the compression along the length of the ankle block 16 is only slightly greater in the rear portion 64 than in front portion 66, due to the off-center application of force. In both the fore and rear ends of spring element 18, the members 22 and 24 are compressed towards each other, with the rear end 80 being slightly more compressed from its original position than the forward end 82. Likewise, stiffeners 52 and 53 are compressed due to the downward application of force. Although this view freezes the compressive stress distribution as such, in reality the weight of the wearer is continually shifting from behind the centerline 70 of the attachment member 34 to forward thereof. Thus, as the wearer continues through the stride, the compression of the ankle block 16 and the elements embedded within travels from the rear portion 64 toward the front portion 66. This migration of the compressed region can be termed "rollover."

In a next snapshot of the walking stride, FIG. 5C shows the prosthetic foot 10 in a "heel-off" position. This is the instant when the wearer is pushing off using ball 72 and toe 74 regions of the foot. Thus, a large compressive force is generated in the front region 66 of the ankle block 16, causing the rear region 64 to experience a large amount of separation or tension. Similarly, the spring element 18 at the rear end 80 expands between the two members 22, 24, while it compresses in the front end 82. The front tip 56 of the foot plate 12 may bend substantially to absorb some of the compressive stresses. Likewise, the front tip 60 of the ankle plate 14 may bend somewhat at this point. It is important to note that although the ankle block 16 absorbs a majority of the compression generated by the wearer, the foot plate 12 and ankle plate 14 are designed to work in conjunction with the resilient ankle block and spring element and provide enhanced dynamic performance. Further, the flexing of the foot plate 12 and ankle plate 14 relieves some of the extreme shear stresses applied to the interfaces between the ankle block 16 and plates, thus increasing the life of the bonds formed therebetween. The stiffener 52 located in the front 66 of the ankle block 16 compresses so as to limit compression of front end 82, giving the wearer balance and to prevent separation of the members 22, 24 from the wedge 28. Stiffener 53 extends due to the separation of ankle block 16 in rear portion 64.

In FIG. 5D, a final position of the walking stride is shown, wherein the prosthetic foot 10 remains in contact with the ground 68, but some of the weight of the wearer is being transferred to the opposite foot, which has now moved forward. In this "toe-off" position, there is less bending of the front tip 56 of the foot plate 12 and less compression of the front portion 66 of the ankle block 16 and front end 82 of spring element 18. Likewise, the front tip 60 of the ankle plate 14 may flex a slight amount, depending on the material and thickness utilized. The region of highest compression of the ankle block 16 remains at the farthest forward region 66, but it is reduced from the compression level of the heel-off position of FIG. 5C. Thus, the rear portion 64 of the ankle block 16 experiences a small amount of tension or spreading.

It can now be appreciated that the "feel" of the present prosthetic foot is greatly enhanced by the cooperation between the foot plate, ankle plate, ankle block and spring inserts. As the wearer continues through the walking stride the dynamic response from the prosthetic foot is smooth as the ankle block with spring inserts compresses in different regions. Further, the flexing of the ankle and foot plates assist in smoothly transmitting the various bumps and jars found in uneven walking surfaces.

Alternative Embodiments

It will be appreciated that alternative embodiments of a prosthetic foot having an ankle block with a spring insert are also encompassed by this invention. One such alternative embodiment is shown in FIG. 6. Reference numerals for FIG. 6 generally correspond to the reference numerals used in FIGS. 1–5D for like elements. Thus, the prosthetic foot 10 shown in FIG. 6 generally comprises a lower foot plate 12 an upper, smaller ankle plate 14, an ankle layer or block 16 made of resilient material, connecting the foot plate 12 to the ankle plate 14, and a spring element 18 embedded within the ankle block. The foot plate 12 has a length and width roughly equal to the approximate length and width of the particular wearer's amputated foot and sized to fit within an outer, flexible cosmesis 30, shown in phantom. As shown in FIG. 6, the ankle plate 14 has a substantially arcuate curvature extending from the integrally formed attachment member 34 to the front of the ankle plate 14.

More particularly, the spring element 18 as illustrated in FIG. 6 is a resilient support member inserted within the resilient ankle block 16. The spring element 18 shown in FIG. 6 is preferably a plate-like member with a curvilinear concave downward shape and a substantially rectangular vertical projection. The spring element 18 is preferably made from a carbon fiber composite material such as described hereinbefore, although other similar materials may be used as well.

The embodiments illustrated and described above are provided merely as examples of certain preferred embodiments of the present invention. Other changes and modifications can be made from the embodiments presented herein by those skilled in the art without departure from the spirit and scope of the invention as defined by a fair reading of the appended claims.

What is claimed is:

1. A prosthetic foot for attaching to a socket or pylon of a lower-limb amputee, comprising:
   a foot plate element having a length approximately equal to the length of a human foot, the foot plate element comprising a resilient material capable of flexing along its length;
   an ankle plate element having a length substantially shorter than the foot plate element;
   an ankle block comprising a relatively soft, compressible material sandwiched between the ankle plate element and the foot plate element, the ankle block providing energy storage and support and connection between the foot plate element and the ankle plate element; and
   a spring element embedded within the ankle block for providing additional energy storage and support, said spring element having a posterior portion configured to compress during heel-strike, and an anterior portion configured to compress during toe-off;
   whereby the foot plate element, the ankle block, and the spring element flex in a cooperative manner to provide substantially smooth and continuous rollover transition from heel-strike to toe-off.

2. The prosthetic foot of claim 1, wherein the foot plate element has a tapered thickness along its length, such that the thickness increases from a heel section to an arch section and decreases from the arch section to a toe section.

3. The prosthetic foot of claim 2, wherein the heel and toe sections are formed substantially concave-up and the arch section is formed substantially concave-down.

4. The prosthetic foot of claim 1, wherein the ankle block has a substantially planar upper surface and a curvilinear lower surface, the upper surface mating with a bottom surface of the ankle plate element, the lower surface mating with a top surface of the foot plate element.

5. The prosthetic foot of claim 1, wherein the ankle plate element, the ankle block and the spring element are centered transversely with respect to and are generally positioned over a back half of the foot plate element.

6. The prosthetic foot of claim 1, wherein the ankle block is made of a foam block having a density between about 150 and 1500 kg/m$^3$.

7. The prosthetic foot of claim 1, wherein the spring element is formed from a carbon fiber composite material.

8. The prosthetic foot of claim 1, wherein the spring element comprises upper and lower relatively flat members secured at their center by a fastener and separated at their ends.

9. The prosthetic foot of claim 8, wherein the upper member is substantially curvilinear concave upward and the lower member is substantially curvilinear concave downward.

10. The prosthetic foot of claim 1, further comprising at least one opening extending through the ankle block adapted to receive a stiffener for adjusting the spring characteristics of the prosthetic foot.

11. The prosthetic foot of claim 10, wherein a first and second cylindrical opening extend through the ankle block, the first opening being positioned in a fore portion of the block and the second opening being positioned in a rear portion of the block.

12. The prosthetic foot of claim 11, wherein tubular stiffeners are placed in the openings.

13. A prosthetic foot, comprising:
   an upper plate;
   a lower plate;
   a compressible layer formed of a compressible material, said compressible material connected to the upper plate and the lower plate and separating the upper plate from the lower plate; and
   a spring element made of resilient material embedded within the compressible layer and spaced apart from the upper and lower plates, said spring element configured to store and release walking energy during ambulation of said prosthetic foot.

14. The prosthetic foot of claim 13, wherein the lower plate has a length and a width roughly equal to the approximate length and width of an amputated foot.

15. The prosthetic foot of claim 13, wherein the upper plate and the compressible layer have approximately the same cross-sectional size.

16. The prosthetic foot of claim 13, wherein the compressible layer is made of a foam material having a density between about 150 and 1500 kg/m$^3$.

17. The prosthetic foot of claim 13, wherein the spring element is made of a carbon fiber material.

18. The prosthetic foot of claim 13, wherein the spring element has a substantially double wishbone shape.

19. The prosthetic foot of claim 13, wherein the spring element is a plate-like member with a curvilinear concave downward shape.

20. The prosthetic foot of claim 13, wherein the spring element is a foam material having a density between about 150 and 1500 kg/m$^3$.

21. The prosthetic foot of claim 13, wherein the spring element is a tubular member inserted into the compressible layer.

22. A prosthetic foot including a resilient ankle block for separably mounting between a foot plate and an ankle plate of a prosthetic foot for providing resilient kinematic support to an amputee relative to a ground surface, the ankle block comprising a block of resilient material and at least one spring insert embedded within the block of resilient material, said spring insert configured to store and release walking energy during ambulation of said prosthetic foot, said ankle block being substantially the sole means of connection and support between said foot plate and said ankle plate.

23. The prosthetic foot of claim 22, wherein the block of resilient material is an expanded polyurethane having a density between about 150 and 1500 kg/M$^3$.

24. The prosthetic foot of claim 23, wherein the expanded polyurethane has a density of about 500 kg/m$^3$.

25. The prosthetic foot of claim 22, wherein a first spring insert comprises upper and lower substantially plate-like members joined at their center and separated at their ends, the upper member being substantially curvilinear concave upward and the lower member being substantially curvilinear concave downward.

26. The prosthetic foot of claim 25, wherein the first spring insert is made of a carbon fiber composite material.

27. The prosthetic foot of claim 25, wherein a second spring insert comprises at least one tubular stiffener.

28. The prosthetic foot of claim 27, wherein a first tubular stiffener is positioned in a fore region of the ankle block between the upper and lower substantially plate-like members, and a second tubular stiffener is positioned in an aft region of the ankle block between the upper and lower substantially plate-like members.

29. The prosthetic foot of claim 28, wherein the first and second tubular stiffeners are made of an expanded polyurethane having a density between about 150 and 1500 kg/m$^3$.

30. The prosthetic foot of claim 29, wherein the first and second tubular stiffeners are made of an expanded polyurethane having a density of between about 250 and 750 kg/m$^3$.

31. The prosthetic foot of claim 22, wherein the at least one spring element is a plate-like member having a substantially curvilinear downward shape.

32. A prosthetic foot, comprising:
   a support plate made of a resilient material and having a length approximately equal to the length of a human foot;
   a layer of compressible material mounted to the support plate; and
   a spring element comprising at least one substantially plate-like member embedded within the layer of compressible material, said plate-like member configured to store and release walking energy.

33. The prosthetic foot of claim 32, wherein the layer of compressible material is foam.

34. The prosthetic foot of claim 32, wherein the spring element is made of a carbon fiber material.

35. The prosthetic foot of claim 32, wherein the spring element comprises a pair of substantially plate-like members, the plate-like members being secured at their center and separated at their ends.

36. The prosthetic foot of claim 32, wherein the at least one substantially plate-like member has a curvilinear concave downward shape.

37. A prosthetic foot for attaching to a socket or pylon of a lower-limb amputee, comprising:
   a foot plate element having a length approximately equal to the length of a human foot, the foot plate element comprising a resilient material capable of flexing along its length;
   an ankle plate element having a length substantially shorter than the foot plate element;
   an ankle block comprising a relatively soft, compressible material sandwiched between the ankle plate element and the foot plate element, the ankle block providing energy storage and support and connection between the foot plate element and the ankle plate element; and
   a spring element embedded within the ankle block for providing additional energy storage and support, said spring element being formed from a carbon fiber composite material;
   whereby the foot plate element, the ankle block, and the spring element flex in a cooperative manner to provide substantially smooth and continuous rollover transition from heel-strike to toe-off.

38. A prosthetic foot for attaching to a socket or pylon of a lower-limb amputee, comprising:
   a foot plate element having a length approximately equal to the length of a human foot, the foot plate element comprising a resilient material capable of flexing along its length;
   an ankle plate element having a length substantially shorter than the foot plate element;
   an ankle block comprising a relatively soft, compressible material sandwiched between the ankle plate element and the foot plate element, the ankle block providing energy storage and support and connection between the foot plate element and the ankle plate element; and
   a spring element embedded within the ankle block for providing additional energy storage and support, said spring element comprising upper and lower relatively flat members secured at their center by a fastener and separated at their ends;
   whereby the foot plate element, the ankle block, and the spring element flex in a cooperative manner to provide substantially smooth and continuous rollover transition from heel-strike to toe-off.

39. The prosthetic foot of claim 38, wherein the upper member is substantially curvilinear concave upward and the lower member is substantially curvilinear concave downward.

40. A prosthetic foot, comprising:
   an upper plate;
   a lower plate;
   a compressible layer connected to the upper plate and the lower plate and separating the upper plate from the lower plate; and
   a spring element made of resilient material embedded within the compressible layer and spaced apart from the upper and lower plates, said spring element being made of a carbon fiber material.

41. A prosthetic foot, comprising:
   an upper plate;
   a lower plate;
   a compressible layer connected to the upper plate and the lower plate and separating the upper plate from the lower plate; and
   a spring element made of resilient material embedded within the compressible layer and spaced apart from the upper and lower plates, said spring element having a substantially double wishbone shape.

42. A prosthetic foot, comprising:

an upper plate;

a lower plate;

a compressible layer connected to the upper plate and the lower plate and separating the upper plate from the lower plate; and an energy storing spring element made of resilient material embedded within the compressible layer and spaced apart from the upper and lower plates, said spring element comprising a plate-like member with a curvilinear concave downward shape.

43. A prosthetic foot including a resilient ankle block for separably mounting between a foot plate and an ankle plate of a prosthetic foot for providing resilient kinematic support to an amputee relative to a ground surface, the ankle block comprising a block of resilient material and at least one spring insert embedded within the block of resilient material, wherein a first spring insert comprises upper and lower substantially plate-like members joined at their center and separated at their ends, the upper member being substantially curvilinear concave upward and the lower member being substantially curvilinear concave downward.

44. The prosthetic foot of claim 43, wherein the first spring insert is made of a carbon fiber composite material.

45. The prosthetic foot of claim 43, wherein a second spring insert comprises at least one tubular stiffener.

46. The prosthetic foot of claim 45, wherein a first tubular stiffener is positioned in a fore region of the ankle block between the upper and lower substantially plate-like members, and a second tubular stiffener is positioned in an aft region of the ankle block between the upper and lower substantially plate-like members.

47. The prosthetic foot of claim 46, wherein the first and second tubular stiffeners are made of an expanded polyurethane having a density between about 150 and 1500 kg/m$^3$.

48. The prosthetic foot of claim 47, wherein the first and second tubular stiffeners are made of an expanded polyurethane having a density of between about 250 and 750 kg/m$^3$.

49. A prosthetic foot including a resilient ankle block for separably mounting between a foot plate and an ankle plate of a prosthetic foot for providing resilient kinematic support to an amputee relative to a ground surface, the ankle block comprising a block of resilient material and at least one energy storing spring insert embedded within the block of resilient material, wherein the at least one spring insert is a plate-like member having a substantially curvilinear downward shape.

50. A prosthetic foot, comprising:

a support plate made of a resilient material and having a length approximately equal to the length of a human foot;

a layer of compressible material mounted to the support plate; and a spring element comprising at least one substantially plate-like member embedded within the layer of compressible material, said spring element being made of a carbon fiber material.

51. A prosthetic foot, comprising:

a support plate made of a resilient material and having a length approximately equal to the length of a human foot;

a layer of compressible material mounted to the support plate; and a spring element comprising a pair of substantially plate-like members being secured at their center and separated at their ends, at least one of said plate-like members being embedded within the layer of compressible material.

52. A prosthetic foot, comprising:

a support plate made of a resilient material and having a length approximately equal to the length of a human foot;

a layer of compressible material mounted to the support plate; and a spring element comprising at least one substantially plate-like member embedded within the layer of compressible material and having a curvilinear concave downward shape.

* * * * *

UNITED STATES PATENT AND TRADEMARK OFFICE
CERTIFICATE OF CORRECTION

PATENT NO.    : 6,206,934 B1
DATED         : March 27, 2001
INVENTOR(S)   : Van L. Phillips It is certified that error appears in the above-identified patent and that said Letters Patent is hereby corrected as shown below:

Title page,
Item [73], Assignee: Flex-Foot, Inc., Aliso Viejo, CA (US) is in error. No assignment was recorded and there is no assignee.

Signed and Sealed this

Twentieth Day of November, 2001

Attest:

NICHOLAS P. GODICI
*Attesting Officer*   *Acting Director of the United States Patent and Trademark Office*